US00PP23279P2

(12) United States Plant Patent
Verwer

(10) Patent No.: US PP23,279 P2
(45) Date of Patent: Dec. 25, 2012

(54) ***DAHLIA* PLANT NAMED 'HDPI117'**

(50) Latin Name: *Dahlia hybrida*
Varietal Denomination: HDPI117

(75) Inventor: Aad W. M. Verwer, Lisse (NL)

(73) Assignee: Veuoer Dahlias B.V., Lisse (NL)

( * ) Notice: Subject to any disclaimer, the term of this patent is extended or adjusted under 35 U.S.C. 154(b) by 97 days.

(21) Appl. No.: 12/932,415

(22) Filed: Feb. 24, 2011

(51) Int. Cl.
*A01H 5/00* (2006.01)

(52) U.S. Cl. ..... Plt./321

(58) Field of Classification Search ..... Plt./321
See application file for complete search history.

*Primary Examiner* — June Hwu

(74) *Attorney, Agent, or Firm* — C. A. Whealy

(57) ABSTRACT

A new and distinct cultivar of *Dahlia* plant named 'HDPI117', characterized by its compact, mounding and dense plant habit; deeply serrated dark-colored leaves; freely flowering habit; daisy-type inflorescence form; large inflorescences with light purple and light pink bi-colored ray florets; and good postproduction longevity.

1 Drawing Sheet

Botanical designation: *Dahlia hybrida.*
Cultivar denomination: 'HDPI117'.

BACKGROUND OF THE INVENTION

The present invention relates to a new and distinct cultivar of *Dahlia* plant, botanically known as *Dahlia hybrida*, and hereinafter referred to by the name 'HDPI117'.

The new *Dahlia* plant is a product of a planned breeding program conducted by the Inventor in Lisse, The Netherlands. The objective of the breeding program is to create new compact container *Dahlia* plants that have dark-colored leaves, large inflorescences and good postproduction longevity.

The new *Dahlia* plant originated from an open-pollination in Lisse, The Netherlands in 2007 of a proprietary seedling selection of *Dahlia hybrida* identified as code number VD5-272, not patented, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled greenhouse environment in Lisse, The Netherlands in 2008.

Asexual reproduction of the new *Dahlia* plant by cuttings since the spring of 2009 in a controlled greenhouse environment in Lisse, The Netherlands, has shown that the unique features of this new *Dahlia* plant are stable and reproduced true to type in successive generations.

SUMMARY OF THE INVENTION

Plants of the new *Dahlia* have not been observed under all possible environmental conditions and cultural practices. The phenotype may vary somewhat with variations in environment such as temperature and light intensity, without, however, any variance in genotype.

The following traits have been repeatedly observed and are determined to be the unique characteristics of 'HDPI117'. These characteristics in combination distinguish 'HDPI117' as a new and distinct *Dahlia* plant:

1. Compact, mounding and dense plant habit.
2. Deeply serrated dark-colored leaves.

3. Freely flowering habit.
4. Daisy-type inflorescence form.
5. Large inflorescences with light purple and light pink bi-colored ray florets.
6. Good postproduction longevity.

Plants of the new *Dahlia* differ primarily from plants of the female parent selection in the following characteristics:

1. Plants of the new *Dahlia* are more compact and denser than plants of the female parent selection.
2. Plants of the new *Dahlia* and the female parent selection differ in ray floret color as plants of the female parent selection have reddish brown-colored ray florets.

Plants of the new *Dahlia* can be compared to plants of the *Dahlia hybrida* 'HS Juliet', disclosed in U.S. Plant Pat. No. 16,907. In side-by-side comparisons conducted in Lisse, The Netherlands, plants of the new *Dahlia* differed from plants of 'HS Juliet' in the following characteristics:

1. Plants of the new *Dahlia* were shorter than plants of 'HS Juliet'.
2. Leaves of plants of the new *Dahlia* were more deeply serrated and darker in color than leaves of plants of 'HS Juliet'.
3. Plants of the new *Dahlia* and 'HS Juliet' differed in ray floret color as plants of 'HS Juliet' had purple-colored ray florets.

Plants of the new *Dahlia* can also be compared to plants of the *Dahlia hybrida* 'Gallery Rubens', not patented. In side-by-side comparisons conducted in Lisse, The Netherlands, plants of the new *Dahlia* differed from plants of 'Gallery Rubens' in the following characteristics:

1. Plants of the new *Dahlia* and 'Gallery Rubens' differed in leaf color as plants of 'Gallery Rubens' had green-colored leaves.
2. Plants of the new *Dahlia* and 'Gallery Rubens' differed in inflorescence form as plants of 'Gallery Rubens' had decorative-type inflorescences.

BRIEF DESCRIPTION OF THE PHOTOGRAPH

The accompanying photograph illustrates the overall appearance of the new *Dahlia* plant. The photograph show the colors as true as it is reasonably possible to obtain in colored reproductions of this type. Colors in the photograph may differ slightly from the color values cited in the detailed botanical description which accurately describe the colors of the new *Dahlia* plant. The photograph comprises a side perspective view of a typical flowering plant of 'HDPI117' grown in a container.

DETAILED BOTANICAL DESCRIPTION

The following observations and measurements describe plants grown during the summer and autumn in 15-cm containers in an outdoor nursery in Lisse, The Netherlands and under conditions and practices which approximate those generally used in commercial *Dahlia* production. During the production of the plants, day temperatures ranged from 15° C. to 30° C. and night temperatures ranged from 10° C. to 20° C. Plants were pinched one time about three weeks after planting. Measurements and numerical values represent averages for typical flowering plants. Plants were four months old when the photographs and description were taken. In the following description, color references are made to The Royal Horticultural Society Colour Chart, 1995 Edition, except where general terms of ordinary dictionary significance are used.

Botanical classification: *Dahlia hybrida* 'HDPI117'.

Parentage:

*Female, or seed, parent*.—Proprietary seedling selection of *Dahlia hybrida* identified as code number VD5-272, not patented.

*Male, or pollen, parent*.—Unknown selection of *Dahlia hybrida*, not patented.

Propagation:

*Type*.—By vegetative cuttings.

*Time to initiate roots, summer*.—About eleven days at soil temperatures of 15° C.

*Time to initiate roots, winter*.—About 13 days at soil temperatures of 15° C.

*Time to produce a rooted young plant, summer*.—About 21 days at soil temperatures of 15° C.

*Time to produce a rooted young plant, winter*.—About 24 days at soil temperatures of 15° C.

*Root description*.—Fine, fleshy; white in color.

*Rooting habit*.—Moderately freely branching; dense.

*Tubers*.—Length: About 15 cm. Diameter: About 15 cm. Texture: Corky. Color: Brownish.

Plant description:

*Plant form/growth habit*.—Compact and mounding plant habit; inverted triangular plant form; freely basal branching with about seven lateral branches per plant; inflorescences held above the foliar plane on strong peduncles; vigorous, bushy and dense growth habit.

*Plant height*.—About 30 cm.

*Plant diameter or spread*.—About 24 cm.

*Lateral branches*.—Length: About 25 cm. Diameter: About 2.1 cm. Internode length: About 7 cm to 20 cm. Texture: Smooth, glabrous. Strength: Strong. Color: Close to 187A; towards the base, tinted with close to 152B.

Foliage description:

*Arrangement*.—Leaves opposite; leaves may be single or compound with three or five leaflets.

*Shape*.—Ovate.

*Apex*.—Acuminate.

*Base*.—Attenuate.

*Margin*.—Deeply serrated, sinuses divergent.

*Length*.—Single leaves: About 4.5 cm. Compound leaves with three leaflets: About 5.3 cm. Compound leaves with five leaflets: About 11 cm.

*Width*.—Single leaves: About 1.9 cm. Compound leaves with three leaflets: About 3.2 cm. Compound leaves with five leaflets: About 9 cm.

*Venation pattern*.—Pinnate.

*Texture, upper and lower surfaces*.—Smooth, glabrous.

*Color*.—Developing leaves, upper surface: Darker than 200A. Developing leaves, lower surface: Close to 147B tinted with close to 187A. Fully expanded leaves, upper surface: Close to 200A; venation, close to 187B. Fully expanded leaves, lower surface: Close to 147B tinted with close to 187A; venation, close to 187A.

*Petioles*.—Length: Single leaves: About 1 mm. Compound leaves with three leaflets: About 6 mm. Compound leaves with five leaflets: About 3 cm. Diameter, all leaves and leaflets: About 1 mm. Texture, upper and lower surfaces: Smooth, glabrous. Color, upper and lower surfaces: Close to 187B.

Inflorescence description:

*Appearance and flowering habit*.—Rotate daisy-type inflorescences with ray and disc florets developing acropetally on a receptacle; inflorescences positioned above and beyond the foliar plane on strong peduncles; inflorescences face mostly upright; freely flowering habit with about 21 inflorescences developing per plant.

*Fragrance*.—None detected.

*Time to flower*.—Plants begin flowering about 65 to 70 days after planting; flower continuously during the summer and autumn in The Netherlands.

*Post-production longevity*.—Good postproduction longevity; inflorescences maintain good substance for about ten days on the plant and for about six days as a cut flower; inflorescences persistent.

*Inflorescence bud*.—Height: About 1.8 cm. Diameter: About 1.6 cm. Shape: Oblate. Color: Close to 187A.

*Inflorescence size*.—Diameter: About 7 cm. Depth (height): About 3.6 cm. Disc diameter: About 1.8 cm. Receptacle height: About 1.6 cm. Receptacle diameter: About 1.9 cm. Receptacle color: Close to 187A.

*Ray florets*.—Length: About 4.2 cm. Width: About 2.4 cm. Shape: Ovate. Apex: Mucronulate. Base: Attenuate. Aspect: Initially upright to roughly perpendicular to the peduncle. Texture, upper and lower surfaces: Smooth, glabrous; velvety.

Number of ray florets per inflorescence: About eight arranged in a single whorl. Color: When opening, upper surface: Close to 77B. When opening, lower surface: Close to 77C. Fully opened, upper surface: Close to 77B; towards the base, close to 73C. Fully opened, lower surface: Ground color, close to 73C; longitudinal ribs, close to 72A.

*Disc florets*.—Shape: Tubular; apex dentate. Length: About 7 mm. Diameter: About 0.8 mm. Number of disc florets per inflorescence: About 40. Color, immature: Apex: Close to 187B. Mid-section: Close to 2C. Base: Close to 2D. Color, mature: Apex: Close to 21A. Mid-section: Close to 2C. Base: Close to 2D.

*Phyllaries*.—Quantity per inflorescence: About five arranged in a single whorl. Length: About 1.7 cm. Width: About 7 mm. Shape: Ovate. Apex: Acute. Base: Attenuate. Margin: Entire. Texture, upper and lower surfaces: Smooth, glabrous. Color, upper and lower surfaces: Close to 200A.

*Peduncles*.—Length: Terminal peduncle: About 9 cm. Fourth peduncle: About 7 cm. Diameter: About 3 mm. Strength: Strong. Aspect: Erect to about 90° from vertical. Texture: Smooth, glabrous. Color: Close to 187A.

*Reproductive organs*.—Androecium, present on disc florets only: Quantity per disc floret: Five. Filament length: About 4 mm. Filament color: Close to 2C. Anther shape: Lanceolate. Anther length: About 3 mm. Anther color: Close to 15A. Pollen amount: Abundant. Pollen color: Close to 21A. Gynoecium, present on ray and disc florets: Quantity per floret: One. Pistil length: About 6 mm. Stigma shape: Lanceolate. Stigma color: Close to 12B. Style length: About 5 mm. Style color: Close to 150C. Ovary color: Close to 150D. Fruits: Length: About 2.2 cm. Diameter: About 1.9 cm. Texture: Smooth, glabrous. Color: Close to 187B. Seeds: Length: About 7 mm. Diameter: About 1 mm. Color: Close to 187B.

Disease/pest resistance: Plants of the new *Dahlia* have not been shown to be resistant to pathogens and pests common to *Dahlia*.

Garden performance: Plants of the new *Dahlia* have exhibited good tolerance to rain and wind and have been observed to tolerate temperatures from about 0° C. to about 35° C. to 40° C.

It is claimed:

1. A new and distinct *Dahlia* plant named 'HDPI117' as illustrated and described.

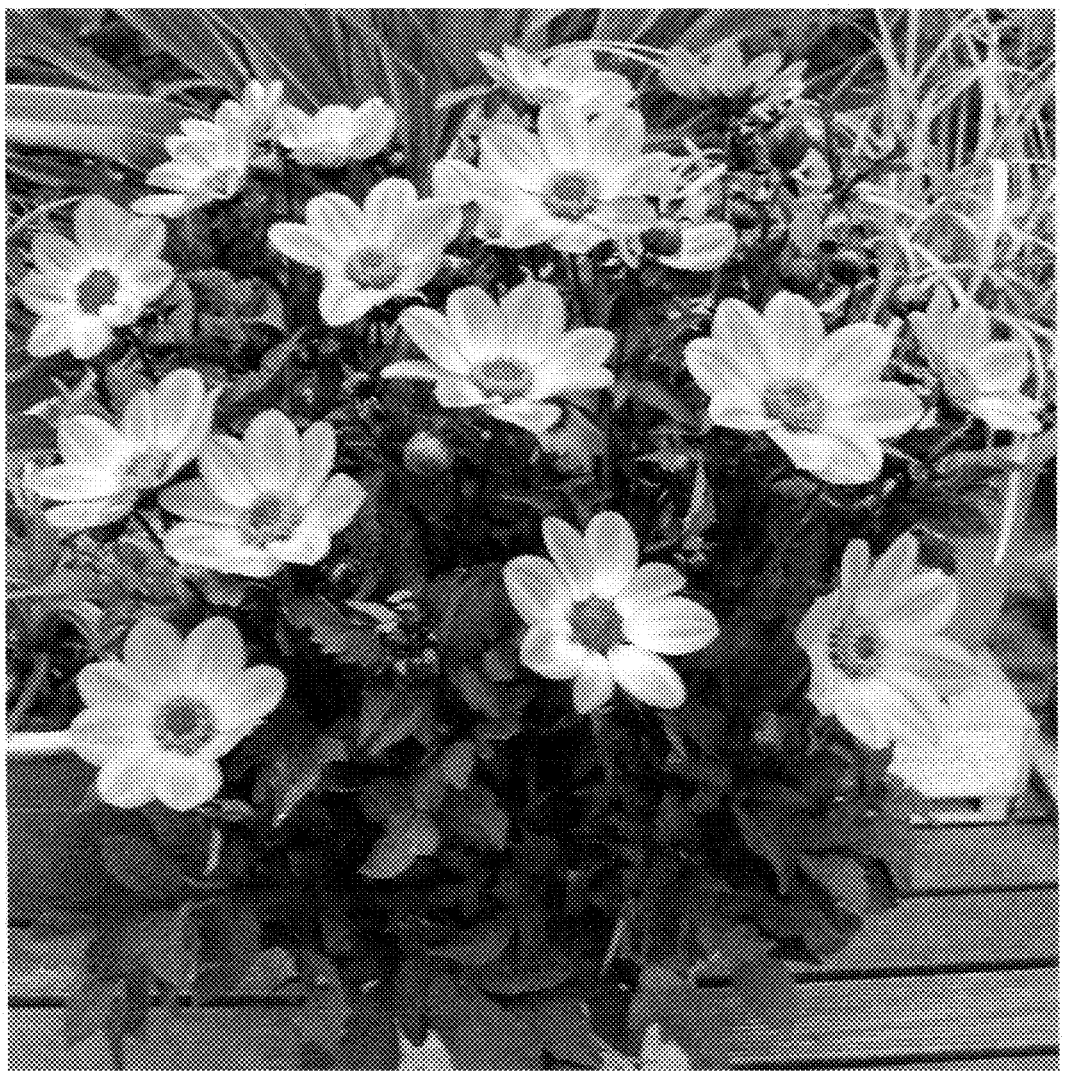

* * * * *